(12) United States Patent
Lee et al.

(10) Patent No.: US 6,748,954 B2
(45) Date of Patent: Jun. 15, 2004

(54) DRUG RELEASE FROM POLYMER MATRICES THROUGH MECHANICAL STIMULATION

(75) Inventors: Kuen Yong Lee, Ann Arbor, MI (US); David J. Mooney, Scio., Township, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 09/983,320

(22) Filed: Oct. 24, 2001

(65) Prior Publication Data

US 2002/0064559 A1 May 30, 2002

Related U.S. Application Data

(60) Provisional application No. 60/243,813, filed on Oct. 27, 2000.

(51) Int. Cl.[7] .......................... A61B 19/00; A61K 9/00; A61K 38/18
(52) U.S. Cl. .................... 128/899; 106/501.1; 128/897; 128/DIG. 12; 424/484; 424/486; 424/488; 514/12
(58) Field of Search ....................... 106/501.1; 128/897, 128/899, DIG. 12; 424/484, 486, 488; 514/12

(56) References Cited

U.S. PATENT DOCUMENTS

| | | | | |
|---|---|---|---|---|
| 5,252,713 A | * | 10/1993 | Morgan et al. | 530/391.7 |
| 5,420,105 A | * | 5/1995 | Gustavson et al. | 514/2 |
| 5,823,198 A | * | 10/1998 | Jones et al. | 128/899 |
| 5,830,207 A | * | 11/1998 | Leeb et al. | 604/890.1 |
| 6,206,914 B1 | | 3/2001 | Soykan et al. | |

FOREIGN PATENT DOCUMENTS

WO     WO 98/12228     *  3/1998

* cited by examiner

*Primary Examiner*—Robert A. Wax
(74) *Attorney, Agent, or Firm*—Millen, White, Zelano, Branigan, P.C.

(57) ABSTRACT

A method for drug delivery and polymer matrix suited to the method are disclosed. The polymer matrix has reversibly bound thereto a drug or combination of drugs, and is capable of releasing the drug or combination of drugs in response to mechanical stimulation of the polymer matrix. According to the method of this invention, such a polymer matrix is delivered to an in vivo locus, for example the site of a wound, trauma, etc., and mechanical stimulation of said polymer matrix is effected in vivo, thereby releasing the drug or combination of drugs in the area of the in vivo locus.

33 Claims, 4 Drawing Sheets

DRUG RELEASE FROM POLYMER MATRICES THROUGH MECHANICAL STIMULATION

Priority is claimed for this invention from U.S. Provisional Application No. 60/243,813 filed Oct. 27, 2000.

STATEMENT REGARDING FEDERALLY SPONSORED RESEARCH OR DEVELOPMENT

This invention was made in the course of research partially sponsored by a grant from the National Institute of Health (NIH) (Grant No. R01 DE13033). The U.S. government has certain rights in the invention.

FIELD OF THE INVENTION

The present invention pertains generally to polymer matrices capable of drug delivery, for instance in tissue engineering applications, and more particularly to such polymer matrices that release drugs or a combination of drugs, such as growth factors, pharmaceuticals, genetic material, etc., in response to mechanical stimulation of the polymer matrix, for instance, compression or tension, induced by any of a variety of mechanisms.

BACKGROUND OF THE INVENTION

An extracellular matrix (ECM) of noncellular material has been identified in many multi-cellular organisms, including-human beings. ECM molecules include specialized glycoproteins, proteoglycans, and complex carbohydrates. A wide variety of ECM structures have been identified, and ECM has been implicated in such biological processes as tissue formation.

Recently, tissue engineering has been widely researched. Tissue engineering is directed towards creating biological tissue rather than relying on scarce transplantable organs. Simply put, the method of tissue engineering is tissue and organ reconstruction using three-dimensional, polymeric matrices, also referred to as "scaffolds", which mimic a body's ECM to provide a space for new tissue formation in vivo. One promising group of materials for making the three-dimensional polymer matrices for tissue engineering are hydrogels. Hydrogels have numerous other applications, including as food additives, blood contact materials, bioadhesives, contact lenses, wound dressings, artificial organs, controlled release formulations, membranes, superabsorbents, cell encapsulation and immunoisolation materials, and delivery carriers for bioactive agents, including drugs. A number of synthetic and naturally derived materials may be used in the formation of hydrogels, and one widely used material is alginate, a hydrophilic polymer derived from seaweeds. Alginate comprises a family of natural copolymers of $\alpha$-D-mannuronic acid and $\beta$-L-guluronic acid. See Martinsen et al., *Biotechnology and Bioengineering*, 33: p. 79–89 (1989); Draget et al., *Carbohydrate Polymers*, 14: p. 159–178 (1991).

Delivery of growth factors from polymer matrices, such as artificial ECM's, is one aspect of tissue engineering that has been the subject of recent research. See Shea et al., *Nature Biotech*, 17: p. 551–554 (1999); and Ripamonti et al., *Crit. Rev. Oral Biol. Med.*, 8: p. 154–163 (1997). Natural ECM's are repositories of various growth factors that are released to cells in surrounding tissue to impact a variety of physiological processes. For instance, the release of vascular endothelial growth factor (VEGF) has been shown to enhance the growth of endothelial cells and promote vascularization of growing tissues. See Neufelf et al., *FASEB J.*, 13: 9–22 (1999). Similar drug delivery can be achieved from synthetic and naturally derived polymers. See Baldwin et al., *Adv. Drug Delivery Rev.*, 33: 71–86 (1998). Most tissues in the body, both human and other animals, are subjected to mechanical stresses, such as occur in the compression of cartilage and muscle tensioning. In many instances, such as exemplified by muscle tensioning, these stresses are mediated by various chemical signals. In other circumstances, such as the compression of cartilage, the mechanical stress is induced by external loading (e.g., leg impact during walking or running). Yet, despite the dynamic conditions under which many body tissues function, drug delivery systems have been designed to operate under static conditions.

It would therefore be advantageous to provide a polymer matrix capable of drug delivery that improves upon conventional drug delivery mechanisms, and particularly one that is more ideally suited to deliver drugs, or combinations of drugs, to dynamic, in vivo environments.

SUMMARY OF THE DISCLOSURE

The present invention relates to a polymer matrix composition, either naturally derived or synthetic, that is capable of releasing a desired drug or combination of drugs into a surrounding environment, including in vivo, when mechanically stimulated by any of a variety of mechanisms, including, without limitation, external loading and chemical signaling. The drug or combination of drugs are reversibly bound to the polymer matrix, so that release of the drug or combination of drugs from the polymer-matrix can be sustained over a period of time and is linked to the mechanical stimulation (e.g., compression, tensioning, etc.) of the polymer matrix. The invention is also directed to methods of drug delivery using the polymer matrix composition. Further aspects of the invention can be seen from reading the full disclosure, and the invention is not limited to specifically denoted aspects.

According to the method for drug delivery of this invention, a polymer matrix is provided having reversibly bound thereto a drug or combination of drugs, the polymer matrix being capable of releasing said drug or combination of drugs when the polymer matrix is mechanically stimulated; the polymer matrix can be delivered to an in vivo locus, including, by way of example, the site of a wound or trauma or disease or malfunctioning tissue in the body of an animal, including human, and mechanical stimulation, originating either outside of or within the animal body, is applied to the polymer matrix to effect release of the drug or combination of drugs in the area of the in vivo locus. As indicated, such mechanical stimulation can be effected by surrounding tissues, such as tensioning muscles, prompted by various chemical signals or other biological pathways. Alternatively, mechanical stimulation can be produced by external factors, for instance, external loading, electromagnetic signals, etc., that act directly on the polymer matrix, or that mediate mechanical stimulation of the polymer matrix by other means. As per one feature of this invention, feedback controlled external means can be employed to mediate the release of a drug or combination of drugs from the polymer matrices. This can take the form, for instance, of a patient-worn device adapted to produce a mechanical stimulation-inducing signal, such as an electromagnetic signal or chemical stimulant, conveyed to the locus of the polymer matrix to effect drug release directly or be mediating an internal mechanical stimulation.

BRIEF DESCRIPTION OF THE DRAWINGS

These and other objects and advantages of the present invention are further understood with reference to the detailed description and the drawings, of which.

DETAILED DESCRIPTION OF THE INVENTION

Figure 1:
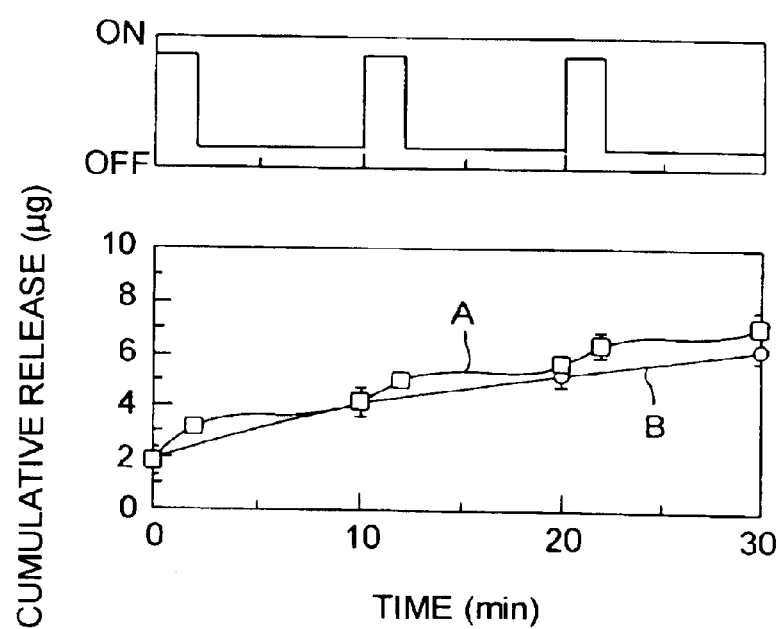
FIG. 1 graphically depicts experimental results of the release of trypan blue from hydrogel polymer matrices in vitro that were subject to mechanical stimulation or no mechanical stimulation.

Referring now to the disclosure as a whole, the present invention will be seen to relate to polymer matrix compositions containing a drug and methods for their employment; but not limited thereto. The inventive polymer matrix has reversibly bound thereto a drug or combination of drugs, the polymer matrix being capable of releasing the drug or combination of drugs when mechanically stimulated. By way of example, such mechanical stimulation may take the form of muscle tensioning in vivo in response to chemically mediated signal pathways, or mechanical stimulation induced by natural means (such as walking or running) or by external factors, for instance external loading, electromagnetic signals and low frequency ultrasound. Eternally generated stimuli are preferred since they can be controlled based on the design and development of external devices. Generally speaking, the polymer matrices of this disclosure may be subject to mechanical stimulation by any of a variety of means sufficient to effect the release of drugs, or a combination of drugs, therefrom, including compression and tensioning of in vivo and external origin, both directly applied and mediated by various means, including chemical signals, electromagnetic signals, repeated tensioning, use of shear force, electrical magnetic field and/or low frequency ultrasound can also be used. In one embodiment, the mechanical stimulation is provided by repeated compression of the polymer matrix composition. For example, the frequency of the repeated compression may be from 0.0001 to 100 Hz and the cycle of compression may be repeated 1 to 100 times per day. Preferably, the mechanical stimulation results in deformation of the polymer matrix, the extent of deformation preferably being equal to 1 to 50% of the original size, i.e., the matrix shrinks by 1% to 50% from the stimulation and then at least partially returns to its original size/shape. Elasticity of the matrix to the mechanical stimulation is preferred. As will be appreciated from the remainder of this disclosure, the degree and kind of mechanical stimulation applied to the polymer matrix in the method of this invention, and the mechanism for producing such stimulation, will depend upon considerations including the in vivo environment where the polymer matrix is provided and the drug release rate desired.

Polymers suited for use in the matrices of this invention include any polymers or copolymers capable of forming elastically deformable matrices that can bind a drug or combination of drugs through specific interactions, including, by way of non-limiting example, ionic bonding or secondary forces; such as hydrophobic bonding, hydrogen bonding or biological receptor binding. One type of biological receptor binding that is useful is ligand-receptor interactions. These polymers may be naturally or synthetically derived. In the particular embodiments described herein as exemplary of the present invention, the polymer matrices comprise three-dimensional alginate hydrogels. "Alginate," as that term is used here, refers to any number of derivatives of alginic acid (e.g., calcium, sodium or potassium salts, or propylene glycol alginate). A preferred example of useful polymers includes natural and synthetic alginates. See e.g., the disclosure of PCT/U.S. Ser. No. 97/16890 filed Sep. 19, 1997, for further description of useful alginate materials, which description is incorporated by reference here. Other hydrogel compositions can be employed which, like alginate hydrogels, form elastically deformable matrices, including, without limitation, chitosan, hyaluronate, collagen, gelatin, dextran, pullulan, poly(2-hydroxyethyl methacrylic acid), poly(N-isopropylacrylamide), poly(ethylene oxide), polyphosphazene, polypeptides, elastomers such as polyurethanes, other polysaccharides, and copolymers of these. Of course, those of skill will understand that other polymers, both naturally derived and synthetic, may be used as the matrices of this invention, according to the requirements of elasticity and drug bonding described herein.

In a preferred embodiment, the polymer matrix comprises an ironically cross-linked alginate. This is preferably of 5,000 to 500,000 daltons molecular weight and is cross-linked with $Ca^{2+}$, $Mg^{2+}$, $Ba^{2+}$ and/or $Sr^{2+}$, ions in a concentration, for example, of 0.1 to 0.5 M. The matrix may be present in the composition in an amount of 1 to 5% by weight.

The polymer matrices used can also be modified to enhance or modify their reversible binding to the drug(s). One way of doing this is to conjugate substances to the polymer matrix which provide biological receptor binding cites to reversibly bind certain drugs. Conjugation of heparin and heparin-like substances to the matrix are particularly useful for this purpose, for example, for providing reversible binding sites for growth factor drugs. Modification of the ionic properties of the matrix to enable or enhance reversible ionic binding to drug(s) having corresponding ionic properties for binding is also useful. Ionic binding between modified alginates as the matrix and anti-cancer drug(s) is one preferred embodiment.

The polymer matrix and its method of application is suitable for use with any drug or combination of drugs that reversibly bind the polymer composition of the matrix by specific interactions such as exemplified above. Preferred reversible binding is ironically or through secondary forces. As used herein, the term "drug" refers broadly to any chemical substance that produces a biological response, including, without limitation, conventional pharmaceuticals, growth factors, and w genetic material. Of course, the drugs or combinations of drugs to be employed will Ma depend upon the biological effect or effects it is desired to elicit. As used in this disclosure, the term "growth factor" refers broadly to any intercellular signaling, locally acting polypeptides that serve to control tissue development and/or maintenance, including, without limitation, platelet-derived growth factors, epidermal growth factors, fibroblast growth factors, insulin or insulin-like growth factors, transforming growth factors, nerve growth factors, and vascular endothelial growth factors (VEGF). Growth factors are a preferred drug for use in the invention, particularly (VEGF), basic fibroblast growth factor (bFGF), platelet-derived growth factor (PDGF), transforming growth factor-beta (TGF-beta) and bone morphogenetic protein (BMP). Other drugs useful in the invention include proteins and anti-cancer drugs.

The entire disclosure of all applications, patents and publications, cited above or below, and U.S. Provisional Application Ser. No. 60/243,813, filed Oct. 27, 2000 are hereby incorporated by reference.

Experimental Results

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

According to each of the illustrated examples, except as otherwise indicated, the polymer matrices comprised alginate hydrogels prepared from a commercially available sodium alginate (PROTANAL LF 20/60) available from Pronova (Drammen, Norway).

EXAMPLE 1

In a first in vitro experiment, alginate hydrogels were prepared comprising 10 g PROTANAL, 4 mg trypan blue (Sigma Chemical) as a model drug molecule, and 63 mg $CaSO_4$ (Sigma Chemical). The hydrogels were cut into disks of approximately 12.7 mm diameter and approximately 2 mm thick, and thereafter swollen overnight in the commercially available Dulbecco's Modified Eagle's Medium (DMEM). The hydrogel disks so prepared were next placed in custom-made sample holders of 13 mm diameter and 30 mm length. Porous stainless steel supports were provided on both the top and bottom of each hydrogel disk to permit release of the trypan blue drug during compression of the hydrogels.

One group of the sample hydrogels were subjected to mechanical stimulation comprising three cycles of compression/relaxation using a mechanical tester (available from MTS, France), according to the following parameters: 10% maximum compressive strain; 2 minutes of compression followed by 8 minutes of relaxation.

A further group comprising control hydrogels, similarly prepared, were not subjected to any mechanical stimulation.

The results of this first, in vitro experiment are shown in FIG. 1, which figure comprises an upper chart graphically depicting the mechanical stimulation cycle of compression/relaxation relative to a lower chart graphically depicting the release of the trypan blue drug from the mechanically stimulated hydrogels (line A). The control, non-compressed hydrogels are also depicted in this lower chart (line B). As can be seen from FIG. 1, release of the trypan blue drug from the compressed (A) hydrogels increased steadily over the course of compression/relaxation cycles. It will further be seen that these results were comparable to the release of the trypan blue drug from the non-compressed (B) hydrogels, indicating that compression did not significantly alter trypan blue release. The inventors speculate that these results are attributable to a failure of the hydrogels to bind the trypan blue, as well as a rapid release of the trypan blue drug from the alginate hydrogels.

EXAMPLE 2

In a second in vitro experiment, alginate hydrogel disks were prepared as discussed above, except that 10 µg vascular endothelial growth factor (VEGF), commercially available from Intergen, as well as radiolabeled VEGF ($^{125}$I-VEGF), available from Biomedical Technologies, were substituted for trypan blue, VEGF being known to reversibly bind with polysaccharides, for instance an alginate hydrogel composition. See Neufeld et al., *FASEV J.*, 13: 9–22 (1999).

The hydrogel disks so prepared were subjected to mechanical stimulation, using the mechanical tester as specified above, for six compression/relaxation cycles (2 minutes of compression followed by 8 minutes of relaxation) at strain amplitudes of 10% or 25%.

A second group comprising control hydrogels, similarly prepared, were not subjected to any mechanical stimulation.

$^{125}$I-VEGF release from the hydrogel disks was quantified with a gamma counter (available from Packard), and converted to absolute protein amounts using the known specific activity of $^{125}$I-VEGF.

Figure 2:
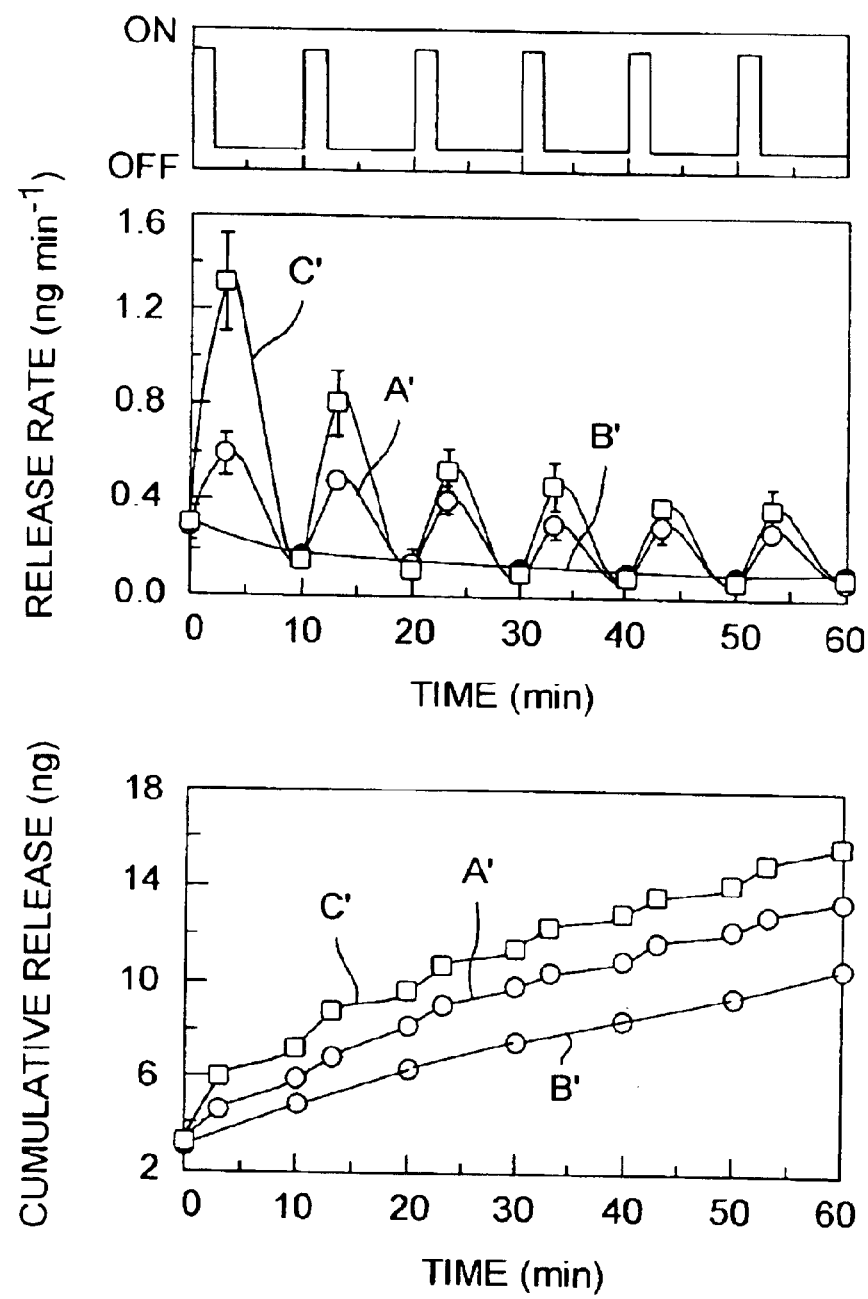
FIG. 2 graphically depicts experimental results of the release rate and cumulative release of the growth factor VEGF from hydrogel polymer matrices in vitro that were subject to mechanical stimulation or no mechanical stimulation.

The results of this second, in vitro experiment are shown in FIG. 2, which figure comprises an upper chart graphically depicting the mechanical stimulation cycle of compressive loading/relaxation relative to both a middle chart and a lower-most chart graphically depicting, respectively, the release rate and cumulative release of VEGF from the hydrogel disks compressed at 10% strain amplitude (line A') and 25% strain amplitude (line C'). The control, non-compressed hydrogels are also depicted (line B'). As can be seen from FIG. 2, the rate of release of VEGF from the compressed (A', C') hydrogel disks was significantly affected by mechanical stimulation, while the control, non-compressed hydrogel disks (B') evidenced a fairly constant release rate over the same time course. The data of FIG. 2 further show that the cumulative release over the same time period for the non-compressed control hydrogel disks (B'). As is also apparent from FIG. 2, the release rate of VEGF was directly related to the magnitude of the mechanical stimulation to which the polymer matrix is subjected.

EXAMPLE 3

In a continuation of the foregoing in vitro experiment, the non-compressed and compressed hydrogel disks were allowed to sit for 24 hours, after which a number of the hydrogels were subjected to further mechanical stimulation cycles of compression/relaxation in the manner described above. A control group of non-compressed hydrogels was also evaluated. The results-of this further evaluation (not shown) were comparable to those date represented in FIG. 2 previously discussed.

EXAMPLE 4

In vivo experimentation was conducted with alginate hydrogel disks comprising 0.5 g Protanal, 10 µg VEGF, and 3.2 mg $CASO_4$. Control disks containing no VEGF were also prepared. The dimensions of these hydrogel disks were 4.8 mm diameter and 2 mm thickness. The hydrogel disks were swollen overnight in DMEM.

Either VEGF or control (non-VEGF) hydrogel disks were subcutaneously implanted in the dorsal region of 7–9 week old severe combined inmmunodeficient (SCID) mice (one disk per test animal). Prior to implantation, the test animals were anesthetized with an intramuscular injection of ketamine (87 mg/mL) and xylazine (2.6 mg/mL). The test animals were allowed a 24 hour recovery period following the implantation surgery.

Using a custom-fabricated mechanical tester, one group of implanted hydrogel disks containing VEGF, as well as one group of hydrogel disks containing no VEGF, were subsequently mechanically stimulated three times daily for a seven (7) day period using a 50% strain amplitude and a compression/relaxation cycle comprising 1 minute of compression followed by 1 minute of relaxation. Two further groups of test animals, one group implanted with hydrogel disks containing VEGF, and one group implanted with hydrogel disks containing no VEGF, were not subject to mechanical stimulation during this test period.

After fourteen (14) days, the test animals were sacrificed and tissue samples taken from the area surrounding the hydrogel disk implants of all test groups (both VEGF and non-VEGF). The tissue samples were fixed in zinc-formalin solution at 4° C. overnight, dehydrated through graded ethanol, embedded in paraff, and cut into 4 $\mu$m sections. These tissue sections were stained with hematoxylin and eosin and microscopically examined (100× and 400× magnifications).

Photomicrographs (100× magnification) of representative tissue sections from the test group animals of this experiment were prepared and examined. The photomicrographs showed the hydrogel disk (A) and the muscle layer (M) in each of the foregoing experiments: (A) for test animals implanted with the control (non VEGF) hydrogel disk, and subject to no mechanical stimulation; (B) for test animals implanted with the control (non VEGF) hydrogel disk, and subject to mechanical stimulation; (C) for test animals implanted with the VEGF-containing hydrogel disk, and subject to no mechanical stimulation; and (D) for test animals implanted with the VEGF-containing hydrogel disk, and subject to mechanical stimulations under the compression/relaxation regimen as described.

Figure 3A:
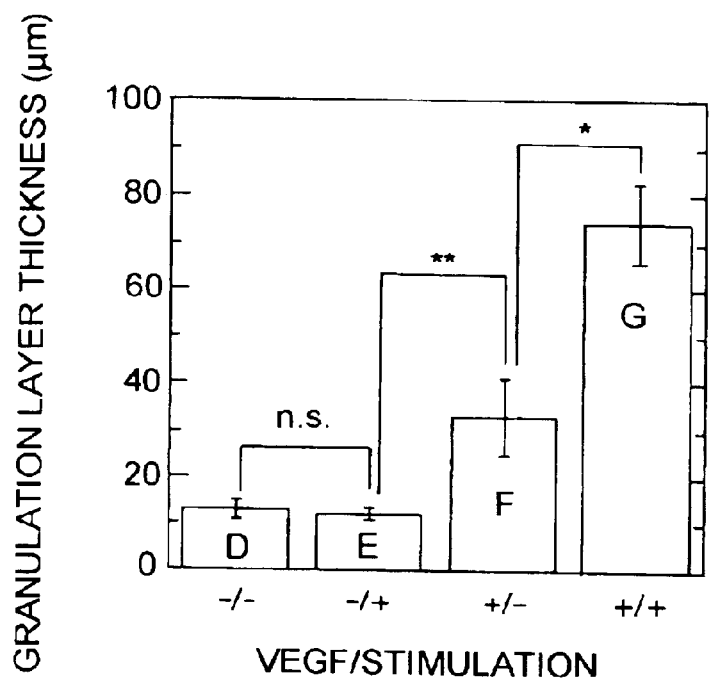
FIGS. 3A–3B graphically depicts blood vessel density and granulation layer thickness for in vivo animal testing of the present invention using the growth factor VEGF released from hydrogel polymer matrices that were subject to mechanical stimulation or no mechanical stimulation.
Figure 3B:
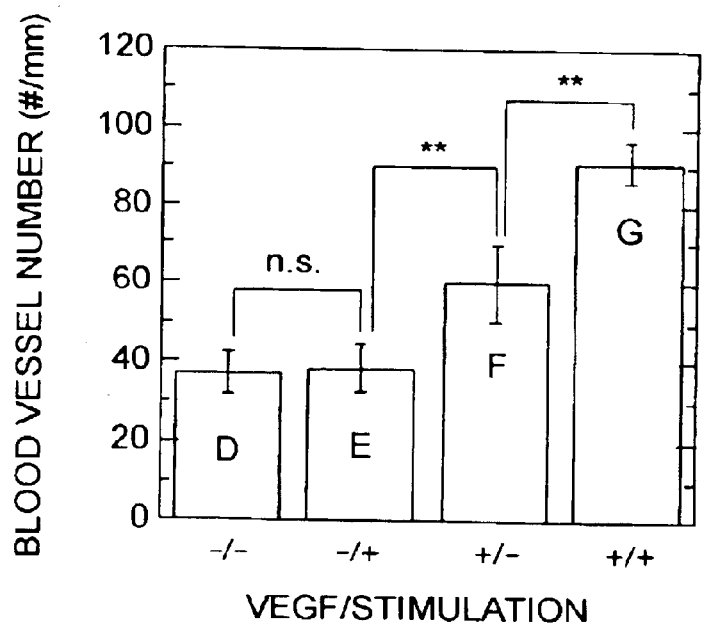

FIGS. 3A and 3B graphically depict granulation layer thickness and blood vessel number, respectively, for test animals in each of the four test groups (i.e., non-VEGF hydrogel/no mechanical stimulation; non-VEGF hydrogel/mechanical stimulation; VEGF hydrogel/no mechanical stimulation; and VEGF hydrogel/mechanical stimulation) for the above-described in vivo experiment. Quantification of granulation layer thickness (given in $\mu$m) was done via microscopic examination (100× magnification), normalized by the interfacial length between the hydrogel and the granulation tissue. Blood vessel density was quantified by capturing digital images of the tissue sections (400× magnification) and analyzing with commercially available NIH Image software. Statistical analysis was done on commercially available INSTAT software.

As seen in FIG. 3A, granulation tissue thickness for test animals implanted with the mechanically stimulated, VEGF-containing hydrogel (bar G) was statistically significantly greater than that for any of the other test groups, including that for test animals implanted with the un-stimulated, VEGF-containing hydrogel (bar F). Granulation tissue thickness for both non-VEGF control groups (one subject to no mechanical stimulation (bar D) and one subject to mechanical stimulation (bar E)) were not statistically different, and were considerably less than the test animals implanted with VEGF-containing hydrogels. Referring next to FIG. 3B, similar results can also be seen for the blood vessel density in animals from these various groups (bars D–G). These results were consistent with the qualitative observations in the photomicrographs.

EXAMPLE 5

A second in vivo experiment was conducted using alginate hydrogel disks comprising 0.5 g Protanal, 10 $\mu$g VEGF, and 3.2 mg $CaSO_4$. Control disks containing no VEGF were also prepared. The dimensions of these hydrogel disks were 4.8 mm diameter and 2 mm thickness. The hydrogel disks were swollen overnight in DMEM.

For this second experiment, the femoral artery of a number of 7–9 week old non-obese diabetic (NOD) mice was ligated and the exposed arterial ends tied off with nylon sutures. Either VEGF-containing or control (non-VEGF containing) hydrogel disks were implanted directly on the ligation site of the mice (one disk per test animal). Prior to implantation, the test animals were anesthetized with an intramuscular injection of ketamine (87 mg/mL) and xylazine (2.6 mg/mL). The test animals were allowed a 24 hour recovery period following the implantation surgery. Using the custom-fabricated mechanical tester referenced above, two groups containing, respectively, were subsequently mechanically stimulated six times daily for a seven (7) day period using a 50% strain amplitude and a compression/relaxation cycle comprising 30 seconds of compression followed by 90 seconds of relaxation. Two further groups of test animals, one group implanted with hydrogel disks containing VEGF, and one group implanted with hydrogel disks containing no VEGF, were not subject to mechanical stimulation during this test period.

After fourteen (14) days, the test animals were sacrificed and tissue samples taken from the area surrounding the hydrogel disk implants (both VEGF containing and non-VEGF containing). The tissue samples were fixed in zinc-formalin solution at 4° C. overnight, dehydrated through graded ethanol, embedded in paraffin, and cut into 4$\mu$m sections. These tissue sections were immunostained with antibodies raised against mouse CD31 (commercially available from Pharmigen) using a terminator blocking solution, universal link secondary antibody, streptavadin-HRP (available from Biocare Medical), and 3,3'-diaminonbenzidine (available from Zymed). This immunostaining technique is known to those skilled in the art. See Nor et al., *Am. J. Pathol.*, 152: 375–384 (1999). These tissue samples were microscopically examined (400× magnification) for blood vessel density (number of vessels/$mm^2$).

Photomicrographs (400× magnification) of representative tissue sections for test animals from groups implanted with VEGF-containing hydrogels were prepared and examined. The hydrogel disk of the test animal (A) was not subjected to mechanical stress according to the regimen described herein, while the hydrogel disk of the test animal (B) was stressed in accordance with the compression/relaxation regimen as stated. In each of the photomicrographs CD31-stained blood vessels were identified.

Figure 4:
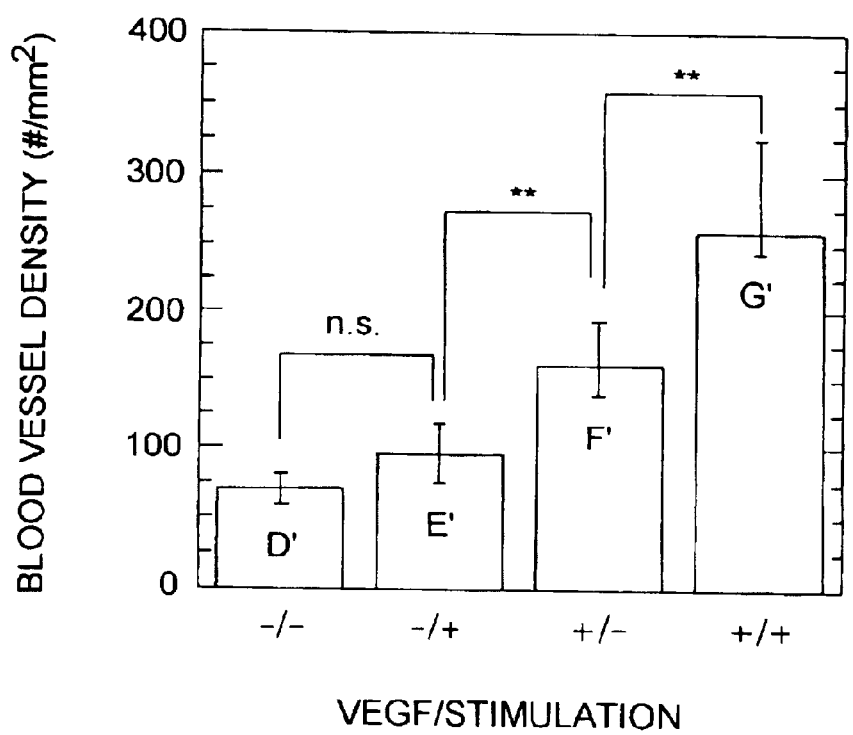
FIG. 4 graphically depicts blood vessel density for in vivo animal testing of the present invention using the growth factor VEGF released from hydrogel polymer matrices that were subject to mechanical stimulation or no mechanical stimulation.

Turning now to FIG. 4, blood vessel density is graphically depicted for test animals in each of the four test groups (non-VEGF hydrogel/no mechanical stimulation; non-VEGF hydrogel/mechanical stimulation; VEGF hydrogel/no mechanical stimulation; and VEGF hydrogel/mechanical stimulation) for the above-described in vivo experiment. As indicated, quantification of blood vessel density was conducted via microscopic examination (400× magnification) and analysis of digital images using commercially available NIH Image software. Statistical analysis was done on commercially available INSTAT software.

As seen in FIG. 4, blood vessel density for test animals implanted with the mechanically stimulated, VEGF-containing hydrogel disks (bar G') was statistically significantly greater than that for any of the other test groups, including that for test animals implanted with the un-stimulated, VEGF-containing hydrogel (bar F'). Blood vessel density for both non-VEGF control groups (one subject to no mechanical stimulation (bar D') and one subject to mechanical (bar E')) were not statistically different, and were considerably less than the test animals implanted with VEGF-containing hydrogels.

While not intended to be limiting of the present invention, it is believed-that drug release from polymer matrices, including those disclosed herein as exemplary, where the drug or combination of drugs reversibly binds the polymer matrix, can be sustained over time as disassociation of the bound drug or drugs replenishes the.

The broad utility of the foregoing invention to drug delivery, tissue engineering, and like applications will certainly be appreciated from this disclosure. Thus, for example, polymer matrices having reversibly bound thereto a drug or combination of drugs may be delivered in vivo to effect locus-specific administration of a drug or combination of drugs in connection with such conditions as vascular diseases or injuries, arthritis, heart diseases and injuries, muscle diseases and injuries, etc.

All references cited to herein and U.S. Provisional Application No. 60/243,813 are explicitly incorporated by reference in their entirety.

Though the foregoing disclosure is made in relation to specific embodiments, it will be understood that the invention as claimed is not so limited, and those skilled in the art will appreciate that various modifications to the described invention are possible without departing from the scope and spirit of this invention, as set forth in the appended claims:

What is claimed is:

1. A polymer matrix composition which comprises a hydrogel polymer matrix having reversibly bound thereto at least one drug, wherein said polymer matrix deforms in shape and/or size and releases said at least one drug in response to mechanical stimulation of said polymer matrix.

2. The polymer matrix composition of claim 1, comprising ironically cross-linked alginate as the polymer matrix.

3. The polymer matrix composition of claim 2, wherein the alginate has a molecular weight of 5,000 to 500,000 daltons.

4. The polymer matrix composition of claim 2, wherein the alginate is present in the composition in a concentration of 1 to 5 wt %.

5. The polymer matrix composition of claim 2, wherein the alginate is ironically cross-linked with $Ca^{2+}$ of 0.1 to 0.5 M.

6. The polymer matrix composition of claim 2, wherein the alginate is ironically cross-linked with $Mg^{2+}$, $Ba^{2+}$ or $Sr^{2+}$.

7. The polymer matrix composition of claim 2, wherein the alginate is also conjugated to heparin or a heparin-like substance which enhances reversible binding of the at least one drug.

8. The polymer matrix composition of claim 1, wherein the polymer matrix comprises a dextran, pullulan, starch, agarose and/or hyaluronate.

9. The polymer matrix composition of claim 1, wherein the polymer matrix comprises a synthetic polymer.

10. The polymer matrix composition of claim 1, wherein the polymer matrix comprises a collagen, gelatin, fibrin and/or modified protein.

11. The polymer matrix composition of claim 1, wherein the polymer matrix deforms and releases said at least one drug in vivo in response to mechanical stimulation of said polymer matrix.

12. The polymer matrix composition of claim 1, wherein the at least one drug is a growth factor.

13. The polymer matrix composition of claim 1, wherein the at least one drug is a vascular endothelial growth factor (VEGF).

14. The polymer matrix composition of claim 1, wherein the at least one drug is a basic fibroblast growth factor (bFGF), platelet-derived growth factor (PDGF), transforming growth factor-beta (TGF-Beta) or bone morphogenetic protein (BMP).

15. The polymer matrix composition of claim 1, wherein the at least one drug is one or more proteins.

16. The polymer matrix composition of claim 1, wherein the at least one drug is one or more anti-cancer drugs.

17. The polymer matrix composition of claim 7, wherein the at least one drug is one or more anti-cancer drugs.

18. The polymer matrix composition of claim 1, wherein the at least one drug is reversibly bound to the polymer matrix through ionic or secondary forces.

19. A method for in vivo drug delivery which comprises mechanically stimulating a polymer matrix composition provided in an in vivo locus, wherein the hydrogel polymer matrix composition comprises a polymer matrix having reversibly bound thereto at least one drug and wherein said polymer matrix deforms in shape and/or size and releases said at least one drug in response to the mechanical stimulation of the polymer matrix.

20. The method of claim 19, wherein the mechanical stimulation is artificially generated in the in vivo locus.

21. The method of claim 19, wherein the mechanical stimulation is naturally generated in the in vivo locus.

22. The method of claim 19, wherein mechanical stimulation is by repeated compression.

23. The method of claim 22, wherein the frequency of the repeated compression is 0.0001 to 100 Hz.

24. The method of claim 22, wherein the cycle of the repeated compression is 1 to 100 times per day.

25. The method of claim 19, wherein the deformation of the polymer matrix by the mechanical stimulation is 1 to 50% of its non-stimulated size.

26. The method of claim 19, wherein the mechanical stimulation is by repeated tension, shear force, electrical magnetic field and/or low frequency ultrasound.

27. The method of claim 19, wherein the mechanical stimulation is controlled by a feedback system.

28. The method of claim 19, wherein the method of drug delivery is part of a method for tissue engineering.

29. The method of claim 19, wherein the method of drug delivery is part of a method for cell transplantation.

30. The composition of claim 1, wherein the composition consists essentially of the polymer matrix having reversibly bound thereto the at least one drug.

31. The method of claim 19, wherein the polymer matrix composition consists essentially of the polymer matrix having reversibly bound thereto the at least one drug.

32. The method of claim 19, wherein the deformation of the polymer matrix by the mechanical stimulation is 10 to 50% of its non-stimulated size.

33. The method of claim 19, wherein the deformation of the polymer matrix by the mechanical stimulation is 10 to 25% of its non-stimulated size.

* * * * *

UNITED STATES PATENT AND TRADEMARK OFFICE
CERTIFICATE OF CORRECTION

PATENT NO. : 6,748,954 B2
DATED : June 15, 2004
INVENTOR(S) : Kuen Yong Lee et al.

It is certified that error appears in the above-identified patent and that said Letters Patent is hereby corrected as shown below:

Column 9,
Lines 47 and 50, reads "ironically" to -- ionically --

Signed and Sealed this

Sixteenth Day of November, 2004

JON W. DUDAS
*Director of the United States Patent and Trademark Office*